US012669507B2

(12) United States Patent
Miller et al.

(10) Patent No.: US 12,669,507 B2
(45) Date of Patent: Jun. 30, 2026

(54) IN VITRO DIAGNOSTIC ASSAY METHODS

(71) Applicant: UCL BUSINESS LTD, London (GB)

(72) Inventors: Ben Miller, London (GB); Leonard Bezinge, London (GB); Peter Dobson, London (GB); Gavin Dold, London (GB); John Morton, London (GB); Rachel Mckendry, London (GB)

(73) Assignee: UCL BUSINESS LTD, London (GB)

( * ) Notice: Subject to any disclaimer, the term of this patent is extended or adjusted under 35 U.S.C. 154(b) by 1229 days.

(21) Appl. No.: 17/273,641

(22) PCT Filed: Sep. 5, 2019

(86) PCT No.: PCT/GB2019/052474
§ 371 (c)(1),
(2) Date: Mar. 4, 2021

(87) PCT Pub. No.: WO2020/049303
PCT Pub. Date: Mar. 12, 2020

(65) Prior Publication Data
US 2022/0011314 A1    Jan. 13, 2022

(30) Foreign Application Priority Data

Sep. 6, 2018    (GB) ..................................... 1814532

(51) Int. Cl.
*G01N 33/58* (2006.01)
*G01N 21/64* (2006.01)

(52) U.S. Cl.
CPC ....... *G01N 33/582* (2013.01); *G01N 21/6428* (2013.01); *G01N 33/587* (2013.01); *G01N 2021/6439* (2013.01)

(58) Field of Classification Search
None
See application file for complete search history.

(56) References Cited

U.S. PATENT DOCUMENTS

| | | |
|---|---|---|
| 9,759,719 B1 | 9/2017 | Acosta et al. |
| 9,897,603 B1 | 2/2018 | Acosta et al. |
| 2006/0008924 A1 | 1/2006 | Anker et al. |
| 2011/0062957 A1 | 3/2011 | Fu et al. |
| 2014/0099007 A1 | 4/2014 | Sarkar et al. |
| 2018/0120219 A1 | 5/2018 | Bumb et al. |

FOREIGN PATENT DOCUMENTS

| | | |
|---|---|---|
| JP | 2012-198058 A | 10/2012 |
| WO | 2004/021004 A1 | 3/2004 |
| WO | 2015/038967 A1 | 3/2015 |
| WO | 2018/048887 A1 | 3/2018 |

OTHER PUBLICATIONS

Armbruster and Pry (2008) "Limit of Blank, Limit of Detection and Limit of Quantitation," Clin Biochem Rev, 29 Suppl 1, S49-52.

Boudou et al. (2009) "High yield fabrication of fluorescent Nanodiamonds," Nanotechnology, 20, 235602.
Bumb et al. (2013) "Silica Encapsulation of Fluorescent Nanodiamonds for Colloidal Stability and Facile Surface Functionalization," J Am Chem Soc, 135, 7815-7818.
Chang et al. (2008) "Mass production and dynamic imaging of fluorescent nanodiamonds," Nat Nanotechnol, 3, 284-288.
Chapman and Plakhoitnik (2013) "Background-free imaging of luminescent nanodiamonds using external magnetic field for contrast enhancement," Opt Lett, 38, 1847.
Cordina et al. (2018) "Reduced background autofluorescence for cell imaging using nanodiamonds and lanthanide chelates," Scientific Reports, 8(1), 4521.
Doronina-Amitonova et al. (2015) "Ultrahigh-contrast imaging by temporally modulated stimulated emission depletion," Opt Lett, 40, 725.
Fu et al. (2007) "Characterization and application of single fluorescent nanodiamonds as cellular biomarkers," PNAS, 104(3), 727-732.
Gong et al. (2017) "A review of fluorescent signal-based lateral flow immunochromatographic strips," J Mater Chem B, 5, 5079-5091.
Gray et al. (2017) "Unravelling the Molecular Basis of High Affinity Nanobodies against HIV p24: In Vitro Functional, Structural, and in Silico Insights," ACS Infect Di., 3, 479-491.
He and Liu (2013) "Paper-Based Microfluidic Device with Upconversion Fluorescence Assay," Anal Chem, 85, 11691-11694.
Hegyi and Yablonovitch (2013) "Molecular Imaging by Optically Detected Electron Spin Resonance of Nitrogen-Vacancies in Nanodiamonds," Nano Lett, 13, 1173-1178.
Hermanson, G.T. "Chapter 5—Homobifunctional Crosslinkers" in Bioconjugate Techniques, 3rd ed. (2013) pp. 275-298.
Igarashi et al. (2012) "Real-Time Background-Free Selective Imaging of Fluorescent Nanodiamonds in Vivo," Nano Lett, 12, 5726-5732.
International Search Report in corresponding International Application No. PCT/GB2019/052474 dated Nov. 20, 2019, 2 pages.
Kong and Yu (2007) "Fourier Transform Infrared Spectroscopic Analysis of Protein Secondary Structures," Acta Biochim Biophys Sin (Shanghai), 39, 549-559.
Krueger et al. (2014) "Biotinylated Nanodiamond: Simple and Efficient Functionalization of Detonation Diamond," Langmuir, 24, 7-8.
Leis et al. (2012) "Simplified digital lock-in amplifier algorithm," Electron Lett, 48, 259.

(Continued)

*Primary Examiner* — Michael D Pak
(74) *Attorney, Agent, or Firm* — Kilpatrick Townsend & Stockton LLP

(57) ABSTRACT

An in vitro diagnostic assay method, comprising: providing a sample which may comprise target analyte(s); contacting the sample with a fluorescent label whose fluorescence can be externally modulated, such that the fluorescent label is associated with target analyte(s), if present, to form a fluorescent label-analyte complex; and detecting the fluorescent label-analyte complex; and device, kit and solid phase for performing an in vitro diagnostic assay method.

6 Claims, 8 Drawing Sheets

Specification includes a Sequence Listing.

(56)            References Cited

OTHER PUBLICATIONS

Mochalin et al. (2011) "The Properties and Applications of Nanodiamonds," Nat Nanotechnol, 7, 11-23.

Mudanyali et al. (2013) "Wide-field optical detection of nanoparticles using on-chip microscopy and self-assembled nanolenses," Nat. Photonics, 7(3), 240.

Paterson et al. (2017) "A low-cost smartphone-based platform for highly sensitive point-of-care testing with persistent luminescent phosphors," Lab Chip, 17, 1051-1059.

Sarkar et al. (2014) "Wide-field in vivo background free imaging by selective magnetic modulation of nanodiamond fluorescence," Biomed Opt Express, 5, 1190-1202.

Shenderova and McGuire (2015) "Science and engineering of nanodiamond particle surfaces for biological applications," Biointerphases, 10, 030802.

Taylor et al. (2017) "Surface functionalisation of nanodiamonds for human neural stem cell adhesion and proliferation," Sci. Rep., 7, 7307.

Walter et al. (2010) "Protein microarrays: Reduced autofluorescence and improved LOD," Eng Life Sci 10, 103-108.

Wu and Weil (2017) "Nanodiamonds for Biological Applications," Phys Sci Rev, 2017, 2, DOI: 10.1515/psr-2016-0104.

Yu et al. (2005) "Bright Fluorescent Nanodiamonds: No Photobleaching and Low Cytotoxicity," J Am Chem Soc, 127, 17604-17605.

Zeng et al. (2018) "Multifunctional Surface Modification of Nanodiamonds Based on Dopamine Polymerization." Langmuir, 34, 4036-4042.

Zhang et al. (2015) "DNA-Based Self-Assembly of Fluorescent Nanodiamonds," J Am Chem Soc, 137, 9776-9779.

Zhao et al. (2014) "Polyglycerol-functionalized nanodiamond as a platform for gene delivery: Derivatization, characterization, and hybridization with DNA," Beilstein J Org Chem, 10, 707-713.

Di(N-succinimidyl) carbonate

▬▬▬ Excitation light (550 nm)
▬▬▬ Emmission light (~675 nm)

(b)

VOLTAGE REGULATOR

| +5 V | DC CONVERTER | | 3 | | LM317 | | 2 | 8.15 V |
| VIN | | 12 V | | VIN | | VOUT | |
| GND | | GND | | | VADJ | | |

240 Ω
1 μF

TCXO
VCC    32 kHz
GND    NC 10 kΩ

4060 COUNTER
VCC    CLOCK
GND    4 Hz 10 kΩ

220 nF 1 kΩ

6     1

+5 V

MW AMPLIFIER
MW OUT    VCC
GND    MW IN

MW VCO
VIN    VTUNE
MW OUT    GND

IN VITRO DIAGNOSTIC ASSAY METHODS

CROSS-REFERENCE TO RELATED APPLICATIONS

The present application is a national stage entry under 35 U.S.C. § 371 of International Patent Application No. PCT/GB2019/052474, filed Sep. 5, 2019, which claims priority to United Kingdom Application No. 1814532.6, filed Sep. 6, 2018, the disclosures of which are hereby incorporated by reference in their entirety for all purposes.

FIELD OF THE INVENTION

The present invention relates to an in vitro diagnostic assay method which comprises using a fluorescent label whose fluorescence can be modulated, such as fluorescent nanodiamonds, in order to detect and/or quantify a target analyte or analytes. The present invention also relates to a device and solid phase for performing such an assay method.

BACKGROUND OF THE INVENTION

There is a need for diagnostic tests for disease diagnosis and monitoring, particularly for in vitro tests which are sensitive enough to offer early diagnosis and accurate monitoring through the identification and quantification of suitable biomarkers. Ultra-sensitive methods to detect biomarkers of disease could lead to major health and economic benefits to patients and populations. Patients will benefit from faster access to treatment leading to better health outcomes, and populations will benefit from reduced risk of disease transmission from communicable diseases, by people who may be unaware of their disease status.

Fluorescence-based lateral flow assays (LFAs) have been extensively investigated with a large variety of nano- and microparticles but are ultimately limited by the background fluorescence from the substrate (e.g. nitrocellulose[1]) and matrix (e.g. serum, blood, saliva, urine, nasal swabs and aspirates, tears, interstitial fluid)[2]. Several approaches have been reported to circumvent this issue, such as the use of upconverting phosphores with infrared excitation[3], or time-gated detection using long-lived fluorescent nanoparticles[4]. However fluorescence-based LFAs with improved sensitivity are still urgently required.

The present inventors have developed a novel method to detect biomarkers for ultra-sensitive in-vitro disease diagnosis using fluorescent labels whose fluorescence can be selectively modulated.

SUMMARY

The present invention provides an in vitro diagnostic assay method, comprising:
  providing a sample which may contain target analyte(s);
  contacting the sample with a fluorescent label whose fluorescence can be externally modulated, such that the fluorescent label is associated with target analyte(s), if present, to form a fluorescent label-analyte complex; and
  detecting the fluorescent label-analyte complex.
  In one embodiment, the assay method further comprises:
  a) exciting the fluorescent label using a suitable light source, and detecting the resulting fluorescence;
  b) modulating the fluorescence of the fluorescent label and detecting the resulting fluorescence to obtain a fluorescence time series comprising the fluorescence results from steps a) and b); and
  c) optionally repeating the modulation step one or more times and detecting the resulting fluorescence to obtain a fluorescence time series comprising the fluorescence results from steps a), b) and c).
  In particular, the assay method may comprise applying a frequency domain analysis, such as a lock-in amplification algorithm or Fourier transform, to the fluorescence time series acquired in step b) or c).
  In one preferred embodiment, the fluorescent label comprises fluorescent nanodiamonds (FNDs).
  The present invention further provides a device for performing an in vitro diagnostic assay, wherein said device comprises:
  a solid phase comprising a fluorescent label whose fluorescence can be externally modulated, such as FNDs;
  an excitation light source;
  a fluorescence modulator; and
  a fluorescence detector.
  In addition, the present invention provides a kit for performing an in vitro diagnostic assay, wherein said kit comprises:
  a solid phase comprising a fluorescent label whose fluorescence can be externally modulated, or
  a solid phase and a separate liquid suspension or solution comprising a fluorescent label whose fluorescence can be externally modulated.
  The present invention also provides a solid phase comprising a fluorescent label whose fluorescence can be externally modulated, such as FNDs, wherein said solid phase is selected from a multiwell plate, beads, column, photonic device, microfluidic chip or capillary bed for microfluidic flow assay.

BRIEF DESCRIPTION OF THE DRAWINGS

FIG. 2: Click chemistry-based DNA functionalisation. Aminated FNDs are modified with an NHS-PEG4-DBCO linker to produce DBCO-terminated FNDs. These can then be reacted with azide-modified DNA, as shown here, or proteins.

The absorbent pad at the top of the strip (13) pulls the fluid through. The nanodiamonds are then detected by lock-in detection using microwave modulation (14).

Figure 5:
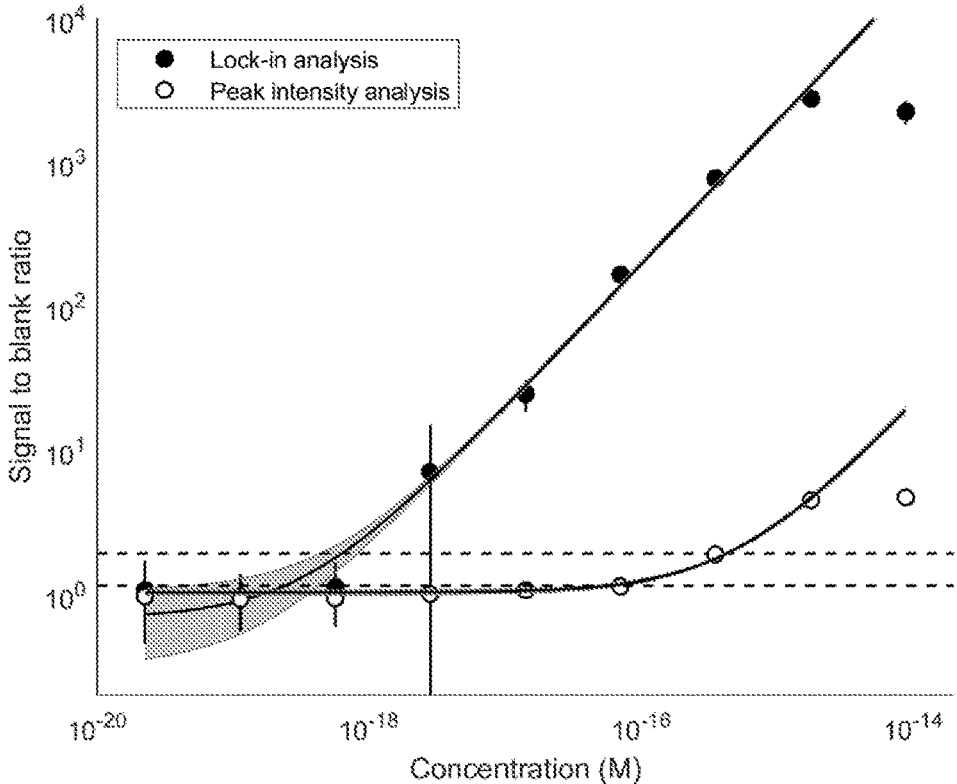

FIG. 5: BSA-biotin limit of detection analysis. Different concentrations of BSA-biotin functionalised 600 nm FNDs were run on poly-streptavidin lateral flow strips. They were analysed by both lock-in amplitude (filled circles) and conventional signal to background intensity analysis (open circles), giving limits of detection of 820 zM and 74 aM respectively.

Figure 6:
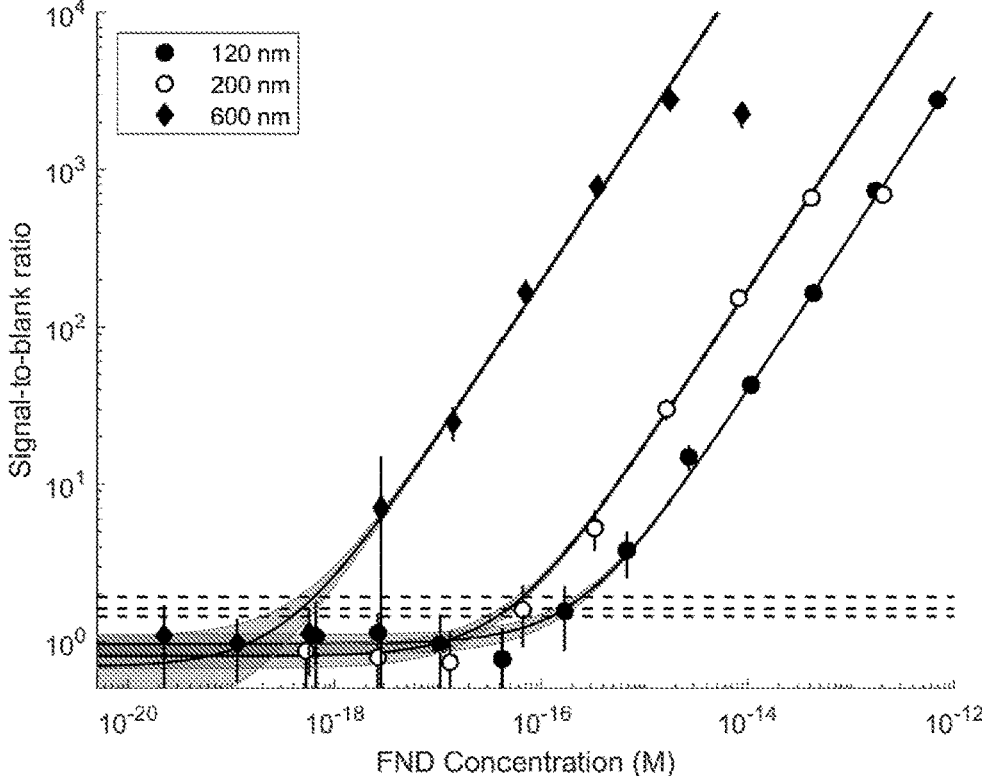

FIG. 6: Fundamental LODs for different size FNDs, using a model biotin-avidin interaction. 55 μL suspensions of BSA-biotin functionalised FNDs are run at different concentrations on poly-streptavidin strips. Serial dilutions are plotted (dots with standard deviations shown as vertical lines) and fitted to linear regression models (solid lines with 95% confidence intervals of the fit shown shaded). Limits of detection for 120 nm (filled circles), 200 nm (open circles), 600 nm (filled diamonds) diameter FNDs are 210 aM, 46 aM, and 820 zM respectively, defined by the intersection of the lower 95% confidence interval of the Langmuir fit with the upper 95% confidence interval of the blanks for each particle size (three sample replicates, and three measurements for each sample).

Figure 7:
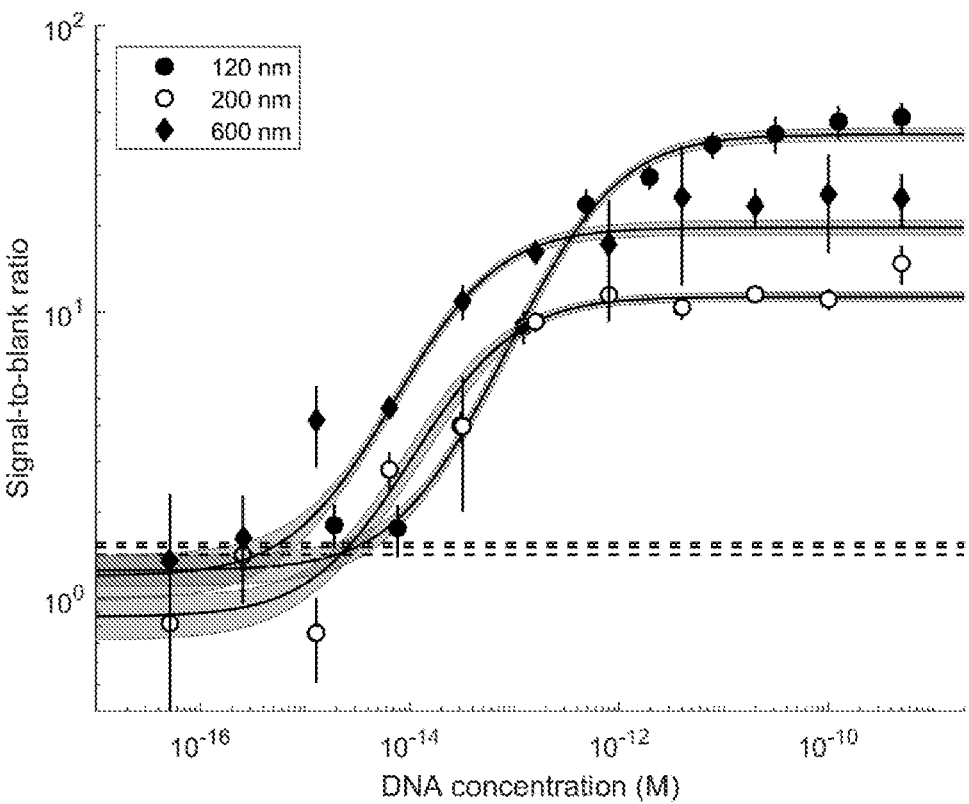

FIG. 7: Proof of concept of detection of recombinase polymerase amplified DNA with FNDs. FNDs are functionalised with an anti-dioxigenin antibody which binds to one end of the model DNA strand. The other end, biotin functionalised, binds to the poly-streptavidin on the lateral flow strip. Three different sizes of FNDs were tested. Serial dilutions are plotted (dots with standard deviations shown as vertical lines) and fitted to the Langmuir adsorption model (solid lines with 95% confidence intervals of the fit shown shaded). Limits of detection for 120 nm (filled circles), 200 nm (open circles), 600 nm (filled diamonds) diameter FNDs are 3.7 fM, 3.6 fM, and 800 aM (corresponding to 480 copies/μL), respectively, defined by the intersection of the lower 95% confidence interval of the Langmuir fit with the upper 95% confidence interval of the blanks for each particle size (three sample replicates, and three measurements for each sample).

Figure 8:
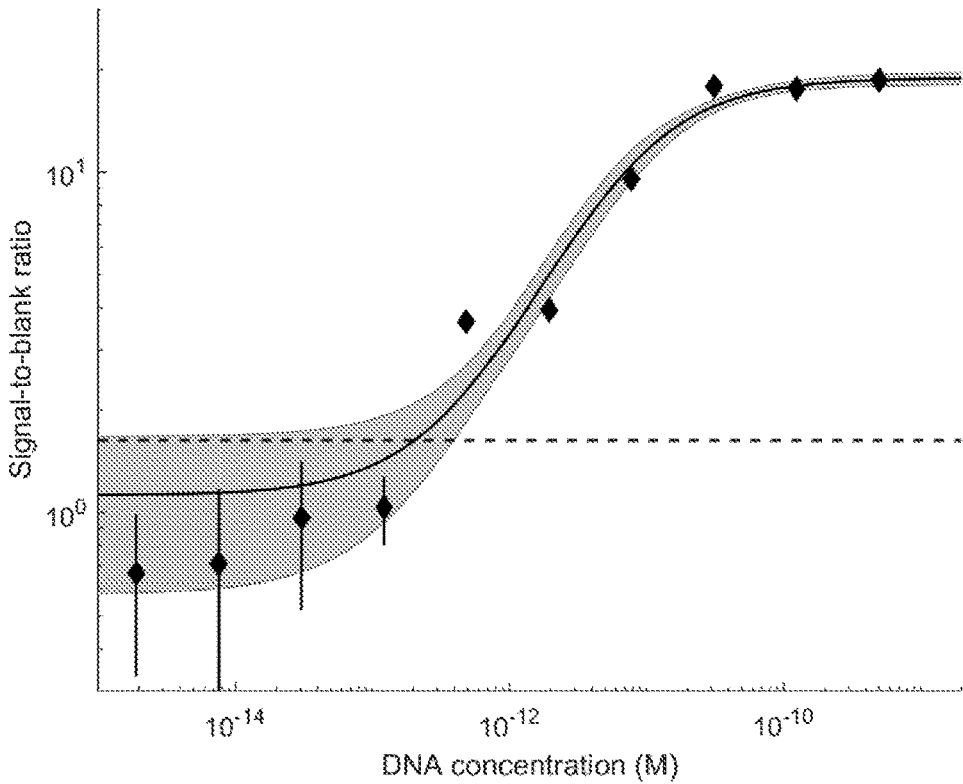

FIG. 8: Proof of concept of direct DNA detection. DNA-functionalised 120 nm FNDs bind to a biotin-modified DNA sequence. The complex then binds to the lateral flow test list, giving a LoD of 400 fM ($\sim 2.4 \times 10^5$ copies/μL).

Figure 9:
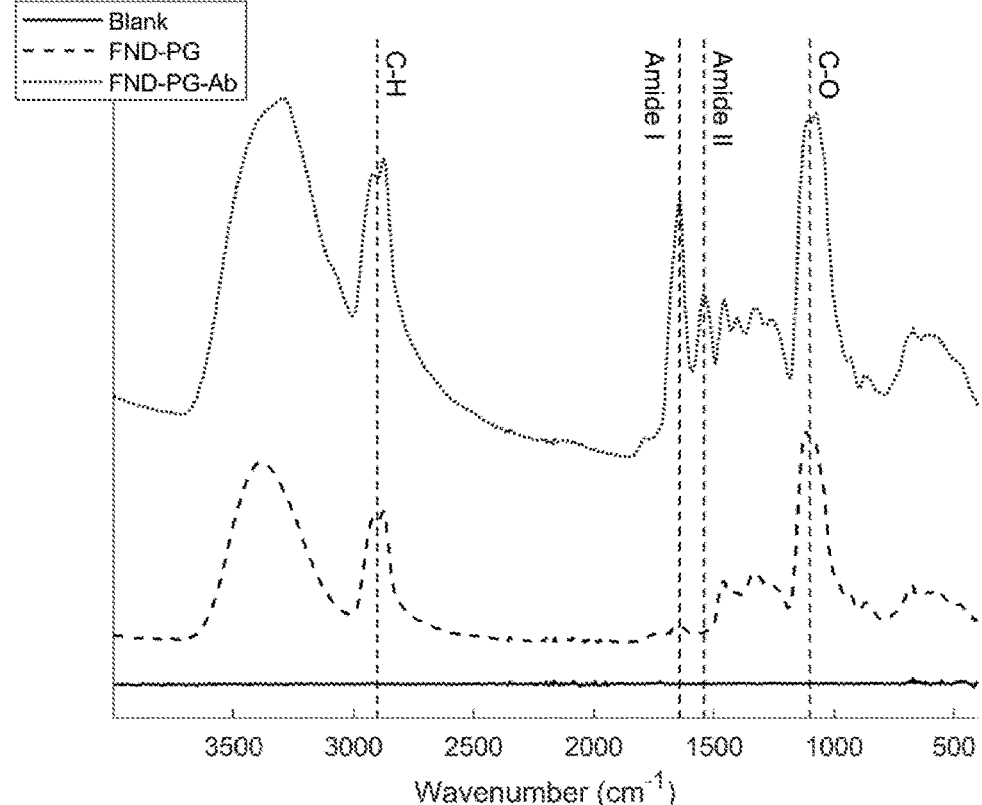

FIG. 9: Fourier transform infrared spectroscopy of FND-PG and antibody (Ab) functionalised FNDs. Both spectra display C—O and C—H vibration bands, indicative of the polyglycerol layer[5]. The antibody functionalised FNDs display additional vibration bands at 1640 cm$^{-1}$ and 1540 cm$^{-1}$, indicative of protein Amide I and Amide II bonds respectively[6].

Figure 10:
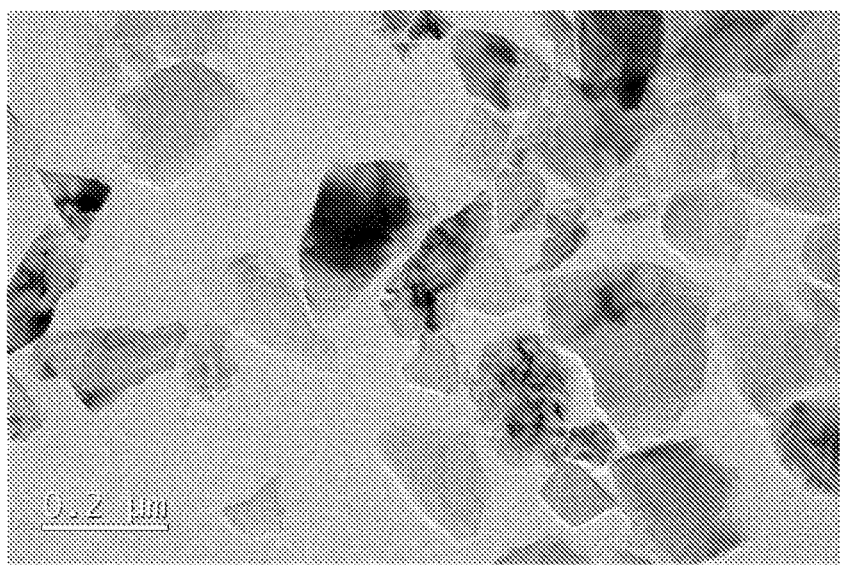

FIG. 10: TEM of antibody functionalised 120 nm FNDs.

Figure 11:
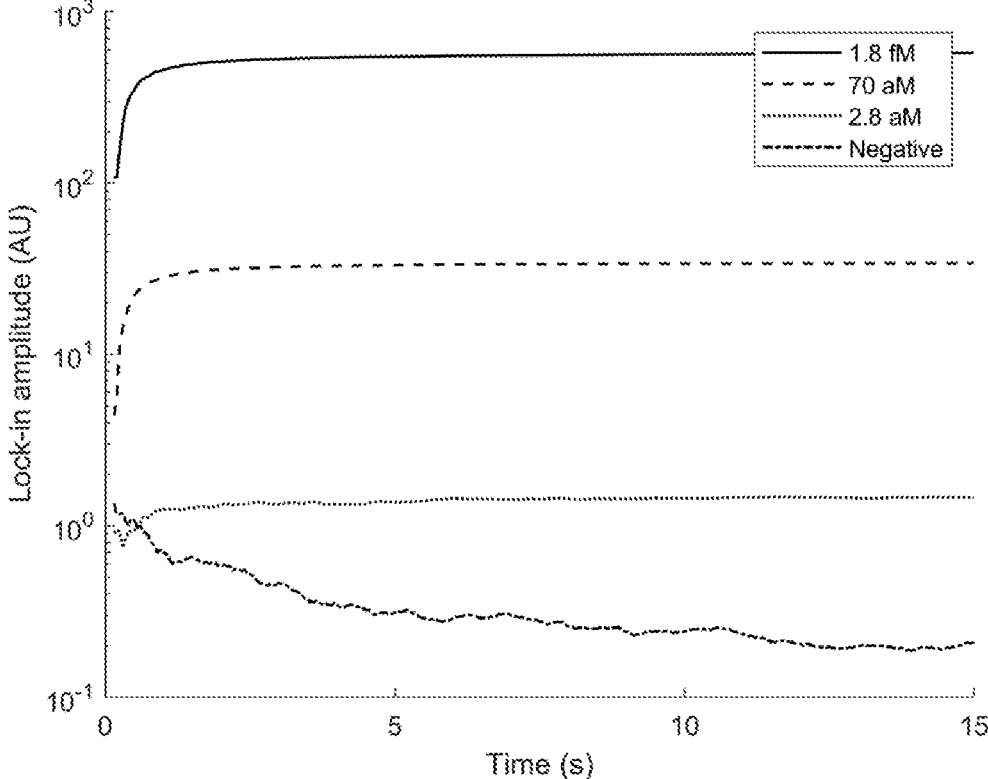

FIG. 11: Time-to-result of lock-in measurements. Variation of lock-in amplitude with time at three positive concentrations of 600 nm FNDs and a negative with a biotin-avidin assay. The results show that positive results quickly reach close to their final value, whilst the negative takes longer to stabilise, reaching within 5% of their 15 second value in 3.9 seconds and 13 seconds respectively. For this reason, 15 second measurements are used.

DETAILED DESCRIPTION OF THE INVENTION

Assay Method

The in vitro assay method of the present invention comprises:

providing a sample which may contain target analyte(s);

contacting the sample with a fluorescent label whose fluorescence can be externally modulated, such that the fluorescent label is associated with target analyte(s), if present, to form a fluorescent label-analyte complex; and detecting the fluorescent label-analyte complex.

The assay method of the present invention may be intended to detect a single target analyte in a sample. Alternatively, the assay method may be for the detection of more than one target analyte, for example a mixture or combination of analytes in a sample.

The target analyte(s) may comprise, for example, a biomarker for disease diagnosis, monitoring or progression, therapeutic drug monitoring, vaccination coverage and vaccine efficacy, forensics, environmental monitoring, foodborne or plant pathogens, serology, monitoring disease treatment, and/or defence applications. For example, the target analytes/biomarker may comprise a peptide, protein, antibody, antigen, carbohydrate, glycopeptide, cell, bacterium, nucleic acid, DNA, RNA, aptamer, cytokine and/or a small molecule. Small molecules are typically defined as less than 1000 Da molecular weight. Examples include hormones, monosaccharides, second messengers, drugs, metal ions, glucose, antibiotics, anaesthetics, vaccine conjugates and steroids; in particular glucose, antibiotics, anaesthetics, vaccine conjugates and steroids. In particular, the target analyte(s) may comprise an antibody, antigen, DNA or RNA.

The fluorescent label of the present invention may be any suitable fluorescent material whose fluorescence can be modulated by an external source. Examples of such materials include dyes and nanomaterials. Suitable organic dyes may include squaraine-derived rotoxane (modulatable for example by an electric field). Suitable nanomaterials include, for example, quantum dots (such as upconverting InAs quantum dots, modulatable with lower energy IR light).

In particular, the fluorescent label may be a material, such as a nanomaterial, which contains a nitrogen vacancy (NV) centre (e.g. one or more NV centres per particle), such as silicon carbide, gallium nitride, aluminium nitride, indium nitride, boron nitride, etc. or fluorescent nanodiamonds (FNDs). In one preferred embodiment, the fluorescent label comprises FNDs.

Thus a preferred method comprises:

providing a sample which may contain target analyte(s);

contacting the sample with fluorescent nanodiamonds (FNDs), such that the FNDs are associated with target analyte(s), if present, to form an FND-analyte complex; and detecting the FND-analyte complex.

FND fluorescence originates from nitrogen-vacancy centres in the diamond lattice, giving them excellent fluorescent properties: they are bright, with no blinking or photobleaching[7,8]. Additionally, they have available surface groups for bio-functionalisation,[9,10] and are easy to mass manufacture[11,12]. Most interestingly, the electron spins of the nitrogen vacancies in the FNDs can be manipulated externally, leading to a reduction in the fluorescence. This can be achieved by magnetic fields (using moving magnets or power-modulated electromagnets),[13,14], electric fields (using electrodes appropriately placed near the sample.), microwaves (using benchtop or portable microwave signal generators),[15,16] or near infra-red (NIR) light (using lasers and optical chopper)[17]. This allows the fluorescence from the FNDs to be selectively modulated, allowing efficient separation from the background fluorescence using a computational lock-in algorithm.[18]

This technique has been used for in-vivo studies with magnetic[13,14] and microwave modulation[15,16] to improve the signal to noise ratio of wide area, high resolution bioimages. FNDs have also been functionalised for various biological assays, such as cellular biomarkers[19,20], proteins[21,22] and DNA though notably not for in-vitro diagnostic applications.[23,24]

The size of the FNDs for use in the present application is not particularly limited and may be, for example in the range 1 nm-10,000 nm, typically 1 nm-1000 nm, preferably 100 nm-800 nm.

The FNDs may be functionalised in order to improve their suitability for the diagnostic assay method, for example to reduce non-specific binding to the substrate and/or bind to the target analyte(s).

Unfunctionalized hydrogen-terminated FND are inherently hydrophobic, which can result in non-specific binding to a substrate, such as for example glass or nitrocellulose paper, potentially leading to low sensitivity, non-specific binding and/or false positives in a diagnostic assay which uses such substrates, such as a paper-based assay. In order to address this, FNDs may be coated with a hydrophilic layer. Thus for example the FNDs may be capped with and/or have adsorbed and/or bound on the surface thereon a suitable compound for increasing the hydrophilicity of the FND, such as a hydrophilic surfactant or hydrophilic polymer. In one embodiment, the hydrophilic layer comprises a hydrophilic polymer, preferably polyglycerol (PG) or polyethylene glycol (PEG). The nature of the PG and PEG is not particularly limited, provided it is suitable for providing a hydrophilic layer on the FNDs. By way of example, short PEG chains of 3 to 15 units, e.g. PEG4, may be used; however longer PEG chains could also be suitable. PG-coated FNDs and other functionalised FNDs are commercially available.

By use of such a hydrophilic layer on the FNDs, non-specific binding and false positives may be reduced, and the sensitivity of the diagnostic assay increased. For paper-based diagnostic assays, polyglycerol-coated FNDs are particularly preferable in view of their low non-specific binding.

FNDs may also be functionalised by attaching a probe suitable for associating with the target analyte. Typically a probe will be designed to associate with, or bind to, a particular target analyte. In some cases, the probe may be suitable for targeting more than one analyte of interest. In other cases, where the assay method is intended to target more than one analyte, it may be desirable to provide a probe for each analyte. This could be achieved by attaching more than one probe to the FNDs, and/or by using a mixture of FNDs with different probes.

For example, suitable probe(s) may comprise a peptide, protein, antibody, nucleic acid, oligonucleotide, aptamer, DNA, RNA, carbohydrate, small molecule or cell. As discussed above, small molecules are typically defined as less than 1000 Da molecular weight. Examples include hormones, monosaccharides, second messengers, drugs, metal ions, glucose, antibiotics, anaesthetics, vaccine conjugates and steroids. Preferred small molecules as probes include those having specific antibodies, such as biotin, digoxigenin, estradiol or other steroids. In one preferred embodiment, the probe(s) may comprise a peptide, protein, antibody, nucleic acid, DNA or RNA. The probe(s) may comprise further components suitable for the diagnostic assay, such as biotin or digoxigenin, which may for example be used to facilitate binding to FNDs and/or the substrate.

The probe(s) may be attached to the FND by means of a suitable surface group. In one preferred embodiment, the probe may be attached to a hydrophilic layer on the FND as described above via a suitable surface group. The probe and FND/hydrophilic layer may be covalently conjugated, for example, using succinimide chemistry[25] for functionalisation with antibodies and DNA for use in direct DNA detection, detection of amplified DNA products, and protein sandwich assays. Another possible method for covalently conjugating the probe and FND/hydrophilic is the use of click chemistry for functionalisation with DNA. Examples of suitable surface groups for use in such methods include an N-hydroxysuccinimide ester group or dibenzocyclooctyne-terminated group.

Figure 1:
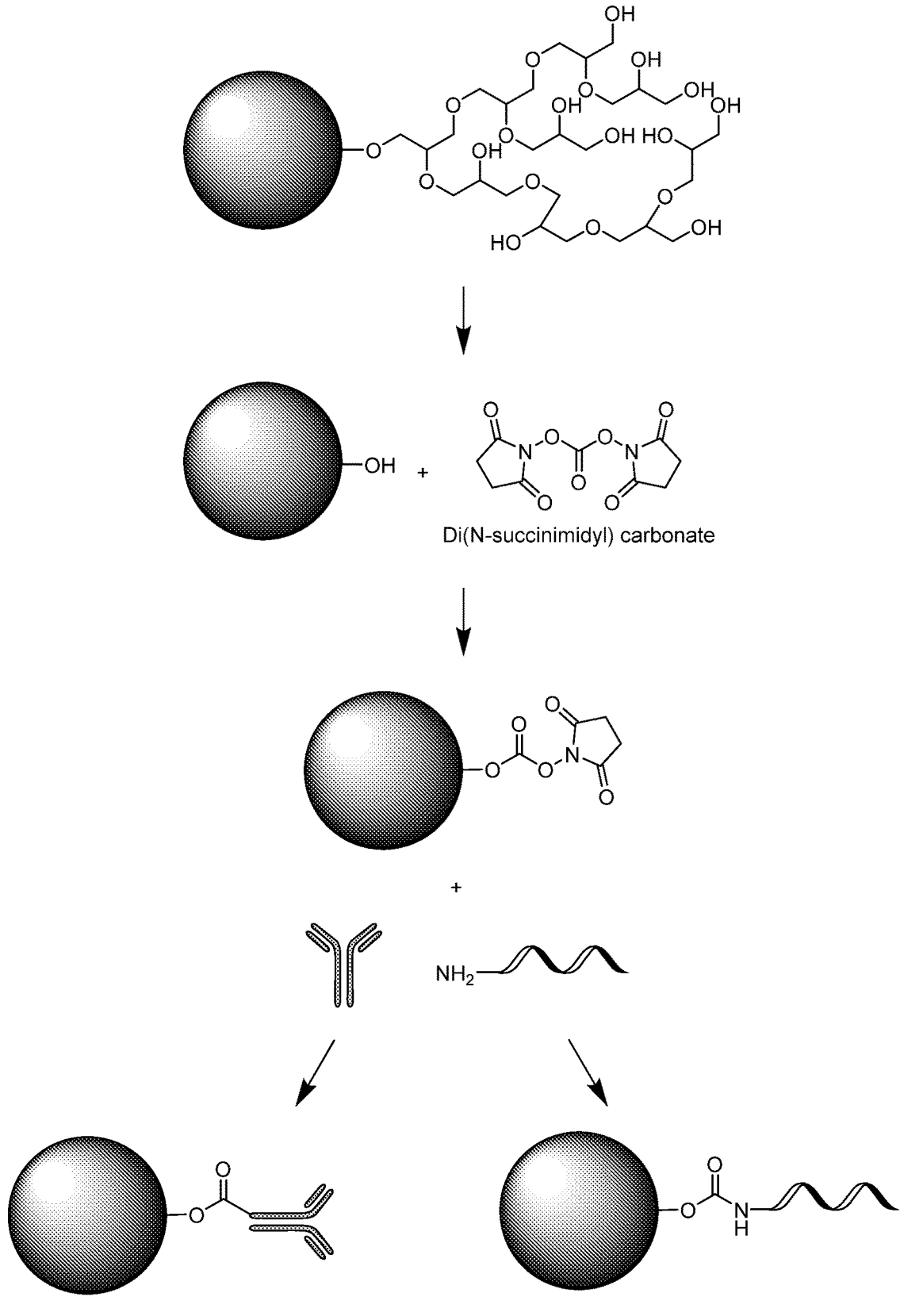
FIG. 1: Schematic of FND functionalisation. PG-capped FNDs are activated with disuccinimidyl carbonate to produce NHS surface groups. These groups are then reacted with antibodies or $NH_2$-functionalised DNA strands.

FIG. 1 shows functionalisation of FNDs with biomolecules using succinimide chemistry. FIG. 1 shows the reaction of the PG layer with disuccinimidyl carbonate to produce N-hydroxysuccinimide (NHS) esters on the surface,[25] which can then bind to antibodies, nanobodies or amine-functionalized DNA.

Figure 2:
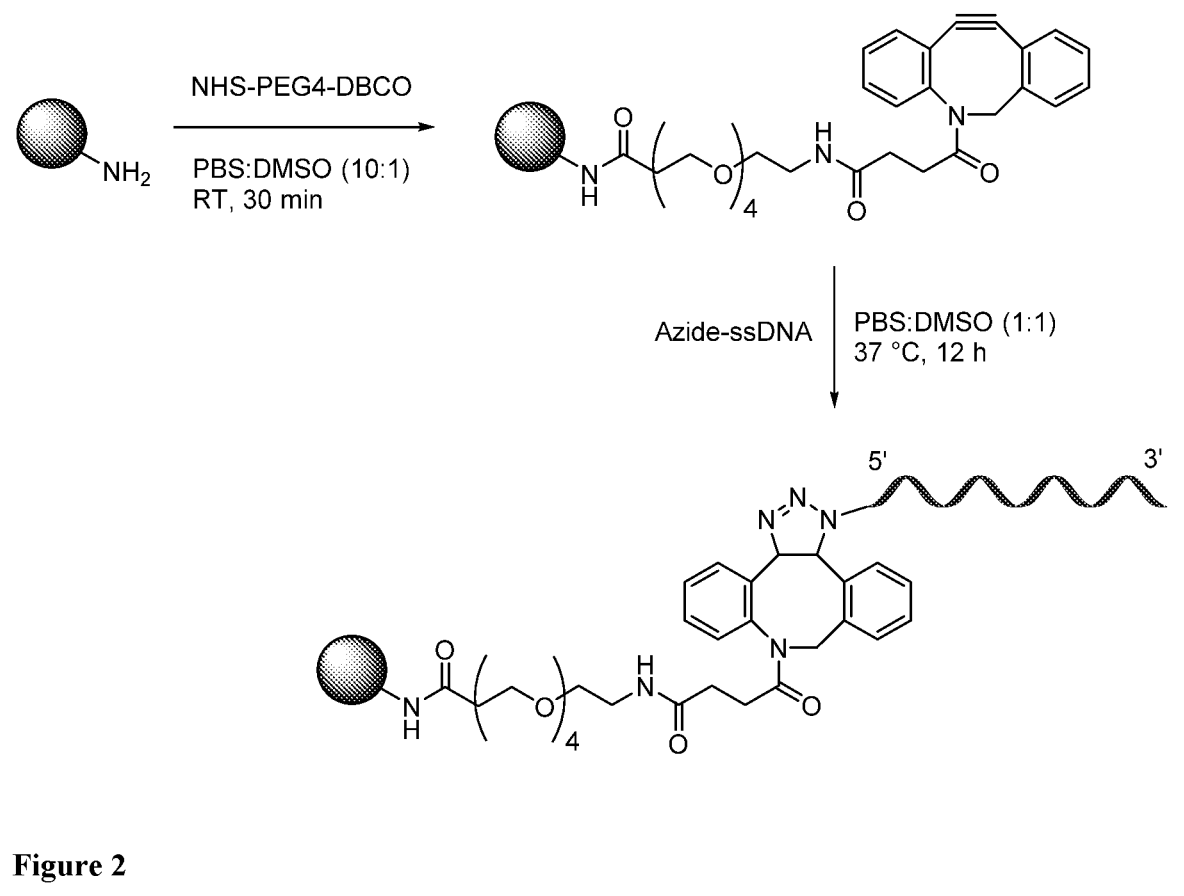

FIG. 2 shows functionalisation of FNDs using click chemistry. FIG. 2 shows the modification of the surface of aminated FNDs with an NHS-polyethylene glycol-dibenzocyclooctyne (NHS-PEG4-DBCO) linker to produce DBCO terminated FNDs. These can be reacted with azide functionalized biomolecules, such as proteins or DNA, as shown.

The fluorescent label will typically be associated with the target analyte by binding to it to form a fluorescent label-analyte complex. For example, the target analyte may form a covalent bond with a group on the surface of the label. In particular, where the fluorescent label is an FND comprising a probe, the target analyte may bind to the probe, for example via a covalent bond.

The fluorescence of the fluorescent label-analyte complex can be detected using any suitable method. Typically, the fluorescence of the complex can be measured using a suitable fluorescence detector, for example by acquiring an image, spectrum or photon count. The fluorescence detector may be, for example a microscope, camera, photodiode detector or a portable reader. The portable reader may be a connected device, such as a smartphone, tablet or other "smart" device. Thus for example the camera of such a reader or device may be used.

In one preferred embodiment, the assay method may further comprise:

a) exciting the fluorescent label using a suitable light source, and detecting the resulting fluorescence;

b) modulating the fluorescence of the fluorescent label and detecting the resulting fluorescence to obtain a fluorescence time series comprising the fluorescence results from steps a) and b); and c) optionally repeating the modulation step one or more times and detecting the resulting fluorescence to obtain a fluorescence time series comprising the fluorescence results from steps a), b) and c).

The "fluorescent label" referred to above may be the fluorescent label alone and/or as part of a fluorescent label-analyte complex, depending on the presence of target analyte. Suitably, the fluorescent label is excited using an appropriate light source (for example an LED or laser) at an appropriate wavelength range. When the fluorescent label has a NV centre, the excitation wavelength range is usually in the visible/NIR range. When the fluorescent label is a FND, the FNDs are suitably excited using a wavelength range of from 450 nm to 640 nm provided by a suitable light source (for example an LED or laser). Preferably the FNDs are excited using a wavelength range of from 520 nm to 580 nm.

The fluorescence of the fluorescent label may be modulated using any means appropriate to the label. Suitable examples include application of a magnetic field, electric field, microwave field or electromagnetic radiation at deep red to near infrared wavelength (for example at a wavelength of 800 nm to 1300 nm). Preferably, the fluorescence is modulated by application of a microwave field or a magnetic field.

In one preferred embodiment, the fluorescent label has a NV centre, in particular the fluorescent label is FNDs, and the fluorescence is modulated by application of a magnetic field, microwave field, or electromagnetic radiation at near infrared or deep red wavelength, preferably by a microwave field or a magnetic field, more preferably by a microwave field.

In one preferred embodiment, the fluorescence may be modulated using an amplitude-modulated microwave field, wherein the amplitude modulation is at 0.1-1000 Hz, suitably 1-10 Hz, and the microwave field is at a frequency of 1-40 GHz, preferably 1-10 GHz, e.g. 1-3 GHz.

For example, when the fluorescent label has a NV centre, in particular the fluorescent label is FNDs, a microwave resonator with resonant frequency of 1-40 GHz may be used to enhance the coupling between the label/FNDs and the applied modulated microwaves. This improved coupling allows the power to be kept low. The microwave resonator may suitably be designed to provide a uniform peak microwave magnetic field amplitude across the label/FNDs, for example using an omega-shaped stripline resonator, capacitively coupled to a microwave feedline or antenna. This allows reduction of noise by averaging over the whole area.

The fluorescence in steps a) to c) of the above method can be detected using a suitable fluorescence detector as described above, for example by acquiring an image, spectrum or photon count. The fluorescence detector may be, for example a microscope, camera, photodiode detector or a portable reader. The portable reader may be a connected device, such as a smartphone, tablet or other "smart" device. By way of example, a camera may be used to acquire an image at each of steps a) to c).

Typically step c) is repeated multiple times (for example 2-1000 times, preferably 50-500, more preferably 100-500 times), preferably at high sampling frequency/short time intervals. Thus suitably images can be recorded using a camera recording frames at frame rates of from 0.1-40,000 fps, typically 10-1000 fps, preferably 10-100 fps, or using an analogue photodetector (for which there is no limit on the frame rate). A typical example would be a 15 second measurement (300 frames at 20 fps, recording up to 60 cycles of the microwave square wave amplitude modulation), as shown in FIG. 11.

The resulting fluorescence time series, comprising for example images, spectra or photon counts, can be analysed to detect and/or quantify the presences of the target analyte(s). Suitably a computer or mobile phone may be used to perform this analysis.

In one preferred embodiment, a frequency domain analysis may be applied to the fluorescence time series acquired in step b) or c). One possibility is a simply image subtraction between field (e.g. magnetic field) "on" and "off". Preferably, a lock-in amplification algorithm or Fourier transform may be applied to the fluorescence time series in order to increase the signal-to-background ratio, thus improving the sensitivity of the diagnostic assay. In particular, a frequency-based analysis can account for drifting of background fluorescence (very low frequency) and remove this from the modulation (higher frequency). It also allows more efficient separation of the signal from background fluorescence, outputting a single lock-in amplitude value at the modulation frequency. Lock-in analysis is computationally efficient, so could be performed quickly by a low-power device. Computational lock-in analysis gives an improved limit of detection over a common benchtop lock-in amplifier as the filters used can be easily adapted to suit this specific application. In addition, when used in conjunction with a paper-based assay, lock-in processing can separate the FND signal from the background fluorescence, and overcome bleaching of the sensor substrate (e.g. paper lateral flow test), thus improving sensitivity and quantification.

EXAMPLE EMBODIMENT

Figure 3:
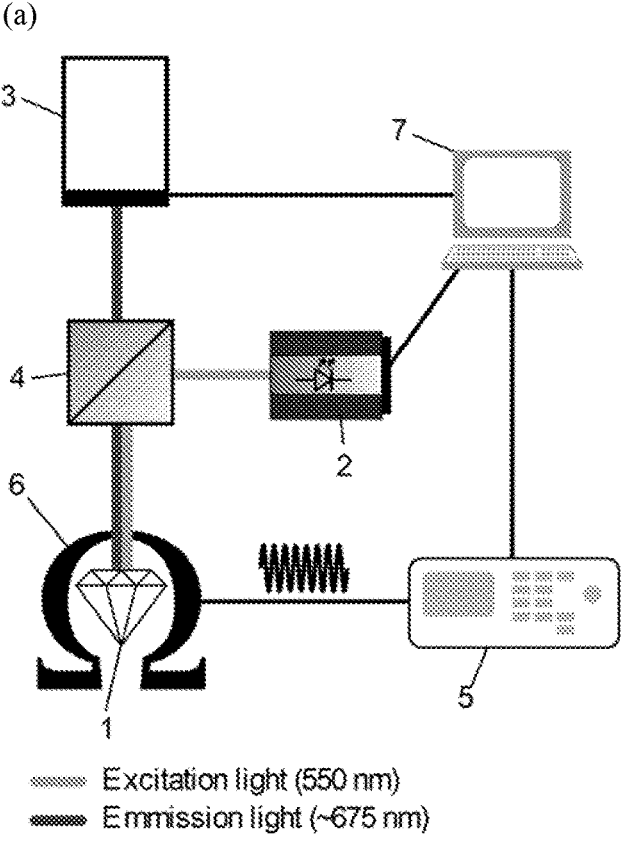
FIG. 3: Microwave modulation of FND fluorescence. (a) Schematic of the system used. FNDs (1) are excited with green light in the 550 nm range using an LED source (2), and emission light (675 nm) is imaged with a CMOS camera (3), after filtering through a filter cube (4). A microwave generator (5) is used to create a signal at 2.87 GHz which is amplitude modulated at 4 Hz to modulate the fluorescence of the FNDs at that frequency. A microwave antenna coupled to an omega-shaped resonator (6) generates the microwave field. All the components are controlled by a computer (7). (b) The circuit schematic of the prototype of a miniaturised modulated microwave generator, replacing the benchtop generator in (a), showing that it can be incorporated into a mobile device.

FIG. 3 shows an example system for implementing the assay method of the present invention. The system shown in FIG. 3 is based around a fluorescence microscope, shown in FIG. 3a, where FNDs (1) are excited with green light (550 nm) using an LED source (2), and the emission (675 nm) is imaged with a CMOS camera (3). The FNDs are simultaneously acted upon by a microwave field, delivered by an omega resonator (6) at 2.87 GHz (quality factor ~100). FIG. 3b shows the miniaturised microwave generation circuit (65×38 mm modulation signal PCB+30×20 mm Oscillator+ 20×20 mm Amplifier). A 4 Hz square wave is generated by a temperature-controlled crystal oscillator and frequency divider. This circuit controls NPN—PNP transistors, which deliver a 12 V square wave to the supply voltage of a voltage-controlled oscillator, set at 2.87 GHz by a voltage regulator. The output of the oscillator is amplified by a small microwave amplifier coupled into the resonator (6), giving an output of a 4 Hz square-wave amplitude modulated microwave field at 2.87 GHz and ~14 dBm. The circuit is powered by 5 V with a maximum current of 220 mA, meaning it could be powered by a USB, battery or smartphone. As the microwaves modulate the fluorescence, the camera records frames at high frame-rates. The mean of each frame is saved, and a computational lock-in-amplification algorithm is applied.

Types of Assay

The diagnostic assay method of the present invention provides excellent sensitivity and flexibility, and is applicable to a range of diagnostic test formats. The assay method may be applied to any suitable in vitro diagnostic assay which can incorporate the use of fluorescent labels. The assay method may comprise, for example, a microfluidic flow assay (including lateral flow assay, dip-stick, vertical flow, microfluidic channels), ELISA, qPCR, microarray, isothermal amplification, dot-blot, flow cytometry or fluorescence-activated cell sorting (FACS). The assay method preferably comprises a microfluidic flow assay (including lateral flow assay, dip-stick, vertical flow, microfluidic channels), ELISA or dot-blot assay, more preferably a microfluidic flow assay (including lateral flow assay, dip-stick, vertical flow, microfluidic channels).

In one preferred embodiment, the assay comprises a solid phase. Thus, the sample which may contain target analyte(s) may be applied to a solid phase, such as a multiwell plate (for example a multiplexed 96-well plate, e.g. of the type used in high throughput laboratory diagnostic methods, such as ELISA), beads, column, photonic device, microfluidic chip or capillary bed for microfluidic flow assay. The solid phase may comprise the fluorescent label (for example the fluorescent label may have been applied to the solid phase in a separate step before application of the sample). Alternatively the fluorescent label may be applied simultaneously with the sample (for example in a liquid solution or suspension comprising both the sample and the fluorescent label), or after the sample (for example in a separate liquid solution or suspension). In a preferred embodiment, the fluorescent label, such as FNDs, is applied to the solid phase before application of the sample. Thus, for example FNDs could be dried onto the solid phase and re-suspended on application of the (liquid) sample. The concentration of the fluorescent label can be optimised using suitable techniques known to one skilled in the art, such as affinity reaction modelling and experimental data.

When the assay comprises a solid phase, the method may comprise one or more steps of washing the solid phase with a liquid reagent and/or using a liquid reagent to run the samples on the solid phase, wherein the liquid reagent may be the same or different in each step. The liquid reagent(s) may comprise suitable surfactant and/or blocking agents or buffers. The surfactant and/or blocking agents or buffers may suitably be selected to reduce non-specific binding to the substrate, in particular for paper-based substrates.

In one embodiment, the assay is a microfluidic flow assay, and the solid phase comprises a suitable capillary bed, such as a microfluidic or porous material selected from paper, nitrocellulose, cellulose, nylon, silk, polyvinylidine fluoride (PVDF), polydimethylsiloxane (PDMS), silicon and glass (for example a glass fibre matrix may be used in lateral flow assays). The microfluidic flow assay may comprise lateral flow, dip-stick, vertical flow or microfluidic channels. In one embodiment, the assay method of the present invention comprises a lateral or vertical flow assay.

In one preferred embodiment, the assay method of the present invention is a microfluidic flow assay, particularly a paper-based assay such as a lateral flow assay or vertical flow assay, which comprises using FNDs as described above as the fluorescent label and applying a lock-in amplification algorithm or Fourier transform in order to lock into the higher frequency signal generated by the FNDs, and filter out the background (low-frequency/DC signal) from the substrate (e.g. paper). This method can overcome some of the inherent limitations of fluorescence detection, which can be limited by the background signal, for example from the fluorescence of paper which can additionally photo-bleach. This new ultra-sensitive method has surprisingly shown sensitivity to detect biomolecular concentrations down to $10^{-19}$ M with biotin-avidin model binding, even in one of the simplest configurations—lateral flow tests. By comparison, the most sensitive commercial lateral flow assays to detect HIV p24 antigen have a reported $2 \times 10^{-13}$ M sensitivity, although direct comparison of sensitivity is challenging given the proprietary antibody/antigen complex and sandwich assay format. The sensitivity of fluorescence-based LFAs has been extensively investigated for more than 15 years and is notoriously limited by the strong background fluorescence of nitrocellulose paper, offering minimal advantage over gold nanoparticle based assays relative to complexity. By contrast the present assays using lock-in detection demonstrate an unexpected enhancement in sensitivity compared to traditional fluorescence measurements, even when compared to prior art reporting the use of nanodiamonds for biomedical in-vivo imaging (see, for example, US 2014/0099007). Thus for example the present inventors have demonstrated up to 620-fold improvement in signal-to-noise ratio (using 600 nm FNDs), leading to a 90-fold improvement in the limit of detection. This increases to an 810-fold improvement in signal-to-noise using 120 nm FNDs, leading to a 380-fold improvement in the limit of detection.

Figure 4:
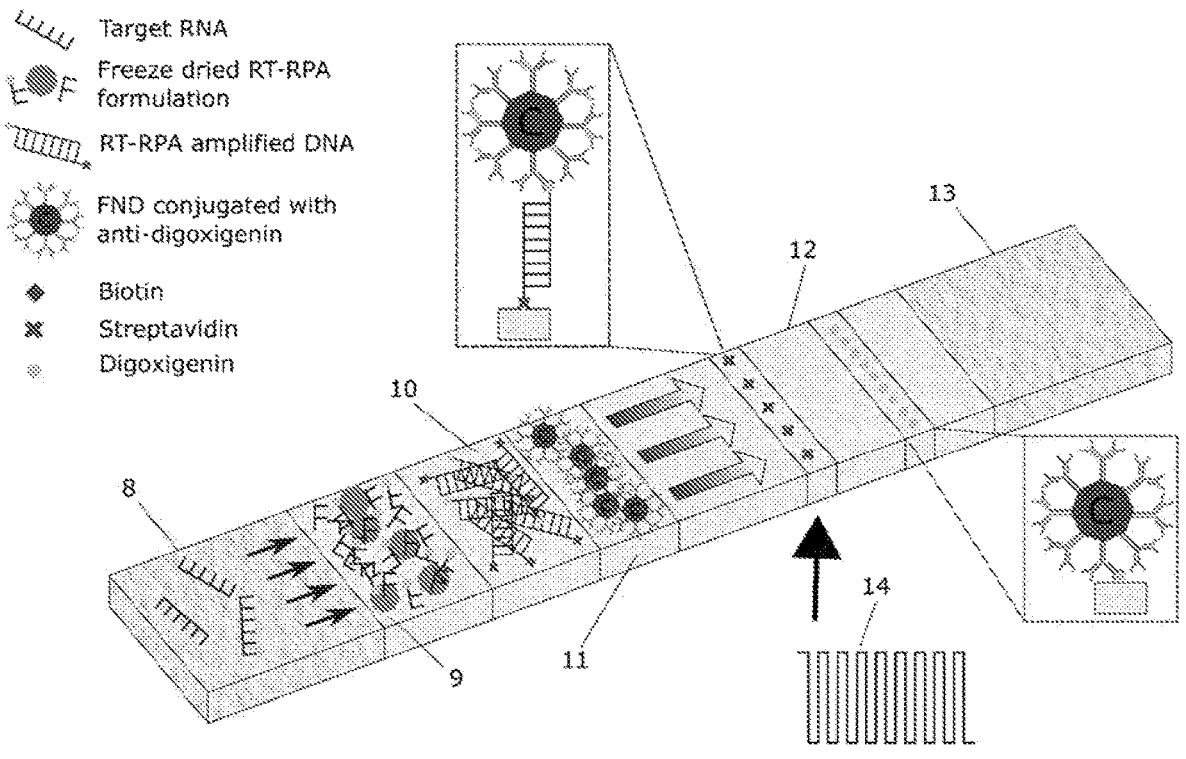
FIG. 4: An example of how nanodiamonds can be used as a label on paper lateral flow microfluidic tests. Target RNA (HIV in this case) is added to the absorbent pad (8). After an optional on-paper isothermal amplification (9), the products (10) bind to a fluorescent nanodiamond in the conjugate pad (11) by a digoxigenin-anti-digoxigenin immunoreaction, and to nitrocellulose paper (12) by biotin-avidin binding.

An example lateral flow assay according to the present invention is shown in FIG. 4.

Device, Kit and Solid Phase

The present invention also relates to a device for performing an in vitro diagnostic assay, such as a device for performing an assay method as described herein, wherein said device comprises:

a solid phase comprising a fluorescent label whose fluorescence can be externally modulated;

an excitation light source;

a fluorescence modulator; and a fluorescence detector.

The solid phase is preferably as described above for the assay method. In particular, the solid phase may be a multiwell plate (for example a multiplexed 96-well plate, e.g. of the type used in high throughput laboratory diagnostic methods, such as ELISA), beads, column, photonic device, microfluidic chip or capillary bed for microfluidic flow assay. The capillary bed for microfluidic flow assay may comprise a microfluidic or porous material selected from paper, nitrocellulose, cellulose, nylon, silk, polyvinylidine fluoride (PVDF), polydimethylsiloxane (PDMS), silicon and glass (for example a glass fibre matrix may be used for lateral flow assays). The microfluidic flow assay may comprise lateral flow, dip-stick, vertical flow or microfluidic channels. In one preferred embodiment, the device is a lateral flow assay or vertical flow assay vertical flow assay device.

The fluorescent label is preferably as described above for the assay method. In particular, the fluorescent label may comprise a material having a nitrogen-vacancy centre as described above in connection with the assay method, such as silicon carbide, gallium nitride, aluminium nitride, indium nitride, boron nitride, etc. or fluorescent nanodiamonds (FNDs). Preferably the fluorescent label comprises fluorescent nanodiamonds (FNDs) as described above. In one embodiment, the FNDs may be functionalised as described above.

The excitation light source may be any light source suitable to provide light at a wavelength suitable to excite the fluorescent label, for example an LED or laser. When the fluorescent label has a NV centre, the excitation wavelength range is usually in the visible/NIR range When the fluorescent label is a FND, the FNDs are suitably excited using a wavelength range of from 450 nm to 640 nm provided by a suitable light source (for example an LED or laser). Preferably the FNDs are excited using a wavelength range of from 520 nm to 580 nm.

The fluorescence detector may be suitable for acquiring an image, spectrum or photon count and may be, for example, a microscope, camera, photodiode detector or a portable reader. In one embodiment, the fluorescence detector may comprise a portable reader. The portable reader may be a connected device, such as a smartphone, tablet or other "smart" device, or a simple bespoke reader. Thus for example the camera of such a reader or device may be used.

The fluorescence modulator may be any means appropriate to modulate the fluorescence of the label. Suitable examples include application of a magnetic field, electric field, microwave field or electromagnetic radiation at deep red to near infrared wavelength (for example at a wavelength of 800 nm to 1300 nm). Preferably, the fluorescence modulator is suitable to apply a microwave field or a magnetic field.

In one embodiment, the fluorescence modulator comprises a microwave signal generator. The microwave signal generator may comprise an oscillator to modulate the signal, and preferably also an amplifier. Amplitude modulation could be generated on-chip or externally, for example using a connected device as described above.

Thus, for example, the fluorescence may be modulated using an amplitude-modulated microwave field, wherein the amplitude modulation is at 0.1-1000 Hz, suitably 1-10 Hz, and the microwave field is at a frequency of 1-40 GHz, preferably 1-10 GHz, e.g. 1-3 GHz.

In one preferred embodiment, when the fluorescent label has a NV centre, in particular when the fluorescent label is FNDs, the device further comprises a microwave resonator with resonant frequency of 1-40 GHz. This can be used to enhance the coupling between the label/FNDs and the applied modulated microwaves, which allows the power of the device to be kept low. The microwave resonator may suitably be designed to provide a uniform peak microwave magnetic field amplitude across the label/FNDs to allow reduction of noise by averaging over the whole area. The microwave resonator may comprise, for example an omega-shaped stripline resonator, capacitively coupled to a microwave feedline or antenna.

Thus electromagnetic microwave modulation may be implemented using a local microwave source connected to an antenna that may (or may not) be attached to or be close to the assay strip. An advantage of using a microwave resonator over, for example moving magnets to generate a magnetic field, is the ability to make a portable device. For example, in an embodiment exemplified by those shown in FIGS. 3 (*a*) and (*b*), a microwave resonator with a small area (1 mm diameter) is positioned below the paper strip and aligned with the test line. The small area and the dry conditions of the detection (as opposed to bioimaging) allows ~6% modulation in fluorescence to be reached, while using a low power, making it suitable for low cost portable smartphone-connected device. Also, microwave modulation does not require moving parts (as opposed to moving magnets), is very compact and can reach higher modulation frequencies compared to using electromagnets (limited by moving parts).

In an alternative embodiment, the fluorescence modulator may comprise means to provide a modulated electric field. An advantage of electric field modulation is that it can be done over a wide frequency range in a very compact space. Electric field modulation may be implemented, for example using a pair of electrodes, across which a high voltage signal of the chosen AC frequency can be applied, adjacent to the assay strip.

Thus the device of the present invention can be miniaturised to a handheld, smartphone-based device to be used for highly sensitive point-of-care (PoC) diagnostics, harnessing the smartphone's processing power, battery power and camera. PoC diagnostics need to meet the ASSURED requirements, and although there are fluorescent-based LFAs they are intrinsically more complicated than colourimetric LFAs (using gold nanoparticles or latex beads) since they require an excitation light source and a detector, for example a portable reader. Moreover, the modulation of FNDs fluorescence reported in the literature has used large benchtop setups to generate powerful magnetic or microwave fields, requiring bulky equipment consuming large amounts of power, and imaging with benchtop optical microscopes. By contrast, the present inventors have demonstrated the modulation of FNDs in a miniaturised system, suitable for rapid and point-of-care settings and requiring low power (USB/battery operated). The presently-claimed device could also be suitable for benchtop diagnostics such as ELISA, and PCR.

The device may further comprise a controller/processing unit, preferably configured to apply frequency-domain analysis to the results obtained from fluorescence detection. Thus, as described above for the assay method, the controller/processing unit may be configured to apply a lock-in algorithm or Fourier Transform to the results obtained from fluorescence detection, as described above in connection with the assay method.

The components of the above-described device may be provided together, or separately as a kit of parts. Thus the present invention also relates to a kit for performing an in vitro diagnostic assay, wherein said kit comprises:

a solid phase comprising a fluorescent label whose fluorescence can be externally modulated, or a solid phase and a separate liquid suspension or solution comprising a fluorescent label whose fluorescence can be externally modulated.

When the kit comprises a solid phase comprising a fluorescent label whose fluorescence can be externally modulated, said solid phase may be as described below, or as described above for the device. In this case, the fluorescent label is applied to the solid phase in a separate step before application of the sample. Thus, for example FNDs could be dried onto the solid phase (e.g. a glass fibre matrix for a lateral flow assay) and re-suspended on application of the (liquid) sample.

When the kit comprises a solid phase and a separate liquid suspension or solution comprising a fluorescent label whose fluorescence can be externally modulated, the solid phase may again be of the type described herein. However in this case the fluorescent label is supplied separately in a liquid suspension or solution. This is then applied simultaneously with the sample (for example in a liquid solution or suspension comprising both the sample and the fluorescent label), or before or after the sample (for example in a separate liquid solution or suspension). In a preferred embodiment, the liquid solution or suspension containing the fluorescent label, such as FNDs, is premixed with the sample before application to the solid phase.

The kit preferably further comprises an excitation light source, a fluorescence modulator and a fluorescence detector as described above for the device, and may also comprise further preferred components as described for the device.

The present invention also relates to a solid phase comprising a fluorescent label whose fluorescence can be externally modulated, wherein said solid phase is selected from a multiwell plate, beads, column, photonic device, microfluidic chip or capillary bed for microfluidic flow assay.

In a preferred embodiment, the fluorescent label comprises a material having a nitrogen vacancy centre as described above in connection with the assay method, such as silicon carbide, gallium nitride, aluminium nitride, indium nitride, boron nitride, etc. or fluorescent nanodiamonds (FNDs). Preferably the fluorescent label comprises fluorescent nanodiamonds (FNDs) as described above. In one embodiment, the FNDs may be functionalised as described above.

The capillary bed for microfluidic flow assay may comprise a microfluidic or porous material selected from paper, nitrocellulose, cellulose, nylon, silk, polyvinylidine fluoride (PVDF), polydimethylsiloxane (PDMS), silicon and glass (for example a glass fibre matrix may be used for lateral flow assays).

The microfluidic flow assay may comprise lateral flow, dip-stick, vertical flow or microfluidic channels.

In one preferred embodiment, the solid phase is a lateral flow assay or vertical flow assay.

All publications and patent applications mentioned in this specification are indicative of the level of those skilled in the art to which this invention pertains.

All publications and patent applications are herein incorporated by reference to the same extent as if each individual publication or patent application was specifically and individually to be incorporated by reference.

Although the foregoing invention has been described in some detail by way of illustration and example for purposes of understanding, it 5 will be clear to those skilled in the art that certain changes and modifications may be practiced within the scope of the appended claims.

The following Examples illustrate the invention.

EXAMPLES

Preparation of Functionalised FNDs

Poly(glycerol) functionalised fluorescent nanodiamonds (FND-PG) were conjugated to single strands of DNA or antibodies using N,N-Disuccinimidyl carbonate (DSC) as crosslinker." In a typical synthesis, 100 μL FND-PG (1 mg mL$^{-1}$, Adamas Nanotechnologies, high brightness FNDs with a 120 nm, 200 nm or 600 nm core, and 20 nm PG layer)) were resuspended in anhydrous N,N-Dimethylformamide (DMF, 99.8%, Sigma-Aldrich) by centrifugation at 21,000 rcf for 7.5 min. After resuspension in DMF, the colloidal solution was sonicated 5 min in an ultrasonic bath. The washing and sonication steps were repeated three times to ensure anhydrous conditions. After the last precipitation, the particles were resuspended in 100 μL of a 50 mg mL-1 solution of DSC (>95%, Sigma-Aldrich) in DMF and stirred for 3.5 hours at 300 rpm and room temperature. Excess reagents were removed through three washing cycles with DMF and the particles resuspended in 100 μL deionized water. Depending on the desired surface modification, aminated oligonucleotides or proteins are added to activated FNDs. The following quantities are for 120 nm core particles, so scale with total surface area (proportional to 1/radius) for other sizes. 5.8 μL of aminated oligonucleotides (500 μm, Integrated DNA Technologies, Inc., 5' Amino Modifier C6-AGCGAC-CGTTCGTCGTACGCTCGGAC) or 13.7 μL of Anti-Digoxigenin antibody (1 mg mL$^{-1}$, Ab-cam plc, ab76907) or 6.8 μL biotinylated Bovin Serum Albumin (BSA-biotin, 2 mg mL$^{-1}$ in deionisedwater, Sigma-Aldrich) were added to the activated FNDs. The mixture was stirred overnight for 15 hours at 300 rpm and room temperature. The reaction was quenched with the addition of 10 μL of Tris-HCl pH 7.5 (1 m, ThermoFisher). After 30 min, the functionalised FNDs were washed three times by centrifugation and resuspension in deionized water and stored in 0.1% BSA in PBS.

Characterisation of Nanoparticles Excitation spectra of the FNDs were acquired with a fluorescence microplate reader (SpectraMax i3, Molecular Devices LLC) and served as a reference to estimate the final FND concentration by comparison of the fluorescence intensity with the stock solution. Emission spectra were recorded with a spectrometer (SPM-002, Photon Control) with a 500 nm LED light source (pE-4000, CoolLED). Dynamic light scattering (DLS) data and zeta potentials were measured with a Zetasizer (Zeta Sizer Nanoseries, Malvern Instruments Ltd) using a 150-fold dilution of the FNDs.

Fourier-Transform Infrared (FTIR) Spectroscopy FTIR spectroscopy was performed by conjugating particles and storing in deionised water, before centrifuging and removing as much water as possible to form a paste which was pipetted onto the FTIR spectrometer (Bruker, Alpha). Six measurements of each sample were taken using 16 reads per measurement. Results are shown in FIG. 9.

Transmission Electron Microscope (TEM)

TEM images of antibody functionalised 120 nm FNDs are shown in FIG. 10.

Lateral Flow Assay

The following assays all use lateral flow strips with a poly-streptavidin test line (Mologic). The strips were 5 mm wide with the test line positioned 7 mm from the bottom of the strip. Experiments were performed using Milk 50% with 0.050% Empigen in deionised water as running buffer and 0.2% BSA with 0.2% Tween 20 in Acetate 10 mm pH 5 as washing buffer. The lateral flow tests were performed by pipetting the solutions to be run into wells of a 96-well plate, then dipping the strips into the wells. All lateral flow assays were performed at room temperature.

Assay with FND-BSA-biotin: BSA-biotin funtionalised FNDs were diluted in running buffer. 55 μL of this suspension was run on each lateral flow strip.

Assay for model RPA products: A single strand of DNA (26 bp), functionalised with digoxigenin at the 3' end and biotin at the 5' end (Integrated DNA Technologies, 5' biotin-GTCCGAGCGTACGACGAACGGTCGCT-digoxigenin 3') was used as a model for RPA amplicons produced with biotin and digoxigenin functionalised primers. These model amplicons were diluted in running buffer and 50 μL of this solution was mixed with 5 μL of anti-digoxigenin antibodies functionalised FND suspension (190 fM, 16 fM, 280 aM in PBS for 120 nm, 200 nm, and 600 nm FNDs, respectively). After 10 minutes at room temperature, these solutions were run on lateral flow strips. After all the solution was run (approximately 10 minutes), the strips were transferred to wells with 75 μL of washing buffer.

Assay for DNA binding: DNA-functionalised FNDs were mixed with 50 μL model DNA strands with a 3' biotin modification (26 bp) in SSC buffer with 100 mM MgCl$_2$ and 125 mM NaCl for a total volume of 56 μL. The solution was heated to 80° C. for 5 minutes, and then cooled over 50 seconds to 66° C., where it was held for 10 minutes, before being cooled to room temperature over a period of 200 seconds. 14 μL of a 5× running buffer (Milk 25%+Empigen 0.25% in deionised water) was added before running on strips. After all the solution was run (approximately 10 minutes), the strips were transferred to wells with 75 μL of washing buffer.

Fluorescence Modulation and Imaging

The paper strips were imaged using a fluorescence microscope (Olympus BX51) with a 550 nm green LED as excitation light source (pE-4000, CoolLED), with a filter cube containing an excitation filter (500 nm bandpass, 49 nm bandwidth, Semrock), a dichroic mirror (596 nm edge, Semrock) and emission filter (593 nm long-pass, Semrock). A 20×/0.4 BD objective (LMPlanF1, Olympus) was used. Images were recorded with a high-speed camera (ORCA-Flash4.0 V3, Hamamatsu) using HCImage Live software (Hamamatsu). All strips were measured when dry.

A microwave field was generated by a Voltage Controlled Oscillator (VCO, Mini-Circuits, ZX95-3360+) and a low noise amplifier (Mini-Circuits, ZX60-33LN+) connected to the resonator circuit board (Minitron Ltd, Rogers 4003C 0.8 mm substrate and 1 oz ft$^{-2}$ copper weight). The resonator was attached to the microscope stage. The tuning voltage of the VCO was set to maximise the decrease in fluorescence. Modulation of the signal was achieved by modulating the input voltage of the VCO with an on-chip reference frequency generator at 4 Hz using a 32.768 kHz Crystal Oscillator (Farnell Ltd, DS32KHZ) with a 14-stage frequency divider (Farnell Ltd, CD4060BM). Circuit board design was performed using EA-GLE (Autodesk). A sweep of modulation frequencies was performed using this VCO and amplifier, using a microcontroller (Arduino Nano 3.0) to generate the different modulation frequencies.

The power dependence of the decrease in fluorescence was recorded using a benchtop microwave generator (HM8135, Rohde & Schwartz Hameg) and a low noise amplifier (Mini-Circuits, ZRL-3500+). A broad sweep of microwave frequencies was measured with RF signal generator (WindFreak Technologies LLC, SynthUSBII).

Computation Lock-In and Limit of Detection

The fluorescence signal was modulated with a modulation frequency signal modulation ($F_m$) and the amplitude of the resulting signal was computed with a phase-sensitive computational lock-in algorithm. Images were recorded with the high-speed camera at a sampling frequency $F_s$. Each frame was averaged to get a mean pixel value at each time point $t_0=0$ to $t_L=L/F_s$, where L was the total number of frames. A moving average low pass filter with a span width of $1.5 \cdot F_s/F_m$ was applied to the fluorescence time series. The filtered signal, $V_{exp}$, was multiplied with a reference signal and its quadrature component to obtain two mixed signals:

$$V_x = V_{exp} \cdot V_{ref} \sin(2\pi F_m t) \quad (1)$$

$$V_y = V_{exp} \cdot V_{ref} \cos(2\pi F_m t) \quad (2)$$

The DC components of these two signals, X and Y, were computed from the mean of $V_x$ and $V_y$, respectively, and enabled the evaluation of the magnitude R of the lock-in amplitude at the frequency $F_m$ according to:

$$R = \sqrt{X^2 + Y^2} \quad (3)$$

Where there was no FND saturation (BSA-biotin), the limit of detection is computed by fitting the lock-in amplitude, as a function of concentration, c, to a linear regression. Where there is saturation (amplicon detection) a Langmuir isotherm was fitted with dissociation constant K, and zero-concentration offset $R_0$:

$$R(c) = \frac{R\infty c}{c + K} + R_0 \quad (4)$$

Fitting was performed in Matlab R2018a using the fitlm and nlinfit functions for linear and Langmuir fits respectively, weighting the fit by the variance a teach concentration. The limit of detection was defined as the intersection of the lower 950% confidence bound of the fit with the upper 95% confidence bound of the blank measurements[28].

Example 1—Lateral Flow Assays

Using the method described above, fluorescent nanodiamonds were functionalised with a probe (protein, antibody, nucleic acid) and used as a marker to detect a target analyte. The complex was captured on a test line for subsequent fluorescent detection. Table 1 summarises lateral flow assays successfully performed with FNDs. Potential applications of the assay are also indicated. The most impactful assays are highlighted with an asterisk (*).

TABLE 1

| Spacer | Conjugated | Target | Capture | Application |
|---|---|---|---|---|
| PG | Biotinylated BSA | — | Streptavidin | Fundamental limit of detection |
| PG | Capricorn anti-HIV1/2 | HIV p24 | VHH antibody-Biotin, Streptavidin | Detection of protein biomarker |
| PG | VHH | HIV p24 | VHH-Biotin (59H10), Strevidin | Detection of protein * biomarker |
| PG | Anti-mouse | HIV p24 | Capricorn anti-HIV1/2, VHH-Biotin, Streptavidin (2 steps) | Detection of protein * biomarker with low affinity antibodies |
| PG | Anti-digoxigenin | 3'-Digoxigenin-ssDNA-Biotin-5' | Streptavidin | Model assay for amplicon detection |
| PG | 5'-NH$_2$-ssDNA | ssDNA-Biotin | Streptavidin | Model assay for amplicon detection. Direct ssDNA detection |
| PEG | 5'-N$_3$-ssDNA | ssDNA-Biotin | Streptavidin | Model assay for amplicon detection. Direct ssDNA detection |
| PG | 5'-NH$_2$-ssDNA | dsDNA-Biotin | Streptavidin | Amplicon detection * with functionalised primers. Direct dsDNA detection. |
| PEG | 5'-N$_3$-ssDNA | dsDNA-Biotin | Streptavidin | Amplicon detection * with functionalised primers. Direct dsDNA detection. |
| PG | Anti-digoxigenin | Digoxigenin-dsDNA-Biotin | Streptavidin | Amplicon detection * with functionalised primers |

Example 2—Fundamental Limit: Biotin-Avidin Binding

The fundamental limits of the assay were established using a biotin-avidin model system. FNDs were functionalized with BSA-biotin on a PG layer, and run at different concentrations on nitrocellulose lateral flow strips with poly-streptavidin on the capture line. The resulting plot is shown in FIG. 5, giving a limit of detection (LoD) of 820 zM (27 particles in 55 uL). This compares to a LoD of 74 aM when using conventional fluorescence intensity analysis (no modulation), giving a 90-fold improvement.

The effect of particle size is shown in FIG. 6. The experiment is repeated with three particle sizes, giving fundamental limits of detection of 210 aM, 46 aM, and 820 zM for 120 nm, 200 nm, 600 nm diameter FNDs respectively, defined by the intersection of the lower 95% confidence interval of the Langmuir fit with the upper 95% confidence interval of the blanks for each particle size.[26]

Example 3—Detection of Amplified DNA Products

Ultrasensitive molecular detection is possible by incorporating isothermal amplification methods into a diagnostic test. The suitability of this system for detecting amplified DNA products was demonstrated based on a dioxigenin-DNA-biotin assay. FNDs were functionalized with anti-dioxigenin antibody on the PG polymer layer, and bound to a dioxigenin on one primer. The other primer was modified with a biotin, which binds to the streptavidin on the test line of the lateral flow strip. Here, a model for amplified products was used: 23 nucleotide DNA strand modified with biotin at the 3' end and digoxigenin at the 5' end. Limits of detection for 120 nm, 200 nm and 600 nm diameter FNDs are 3.7 fM, 3.6 fM, and 800 aM (corresponding to 480 copies/μL), as show in FIG. 7. This is more sensitive than any lateral flow assay that we have found in the literature without amplification. We hope to achieve single molecule detection incorporating the isothermal amplification, and have already demonstrated detection of products from recombinase polymerase amplification (Table 1).

Example 4—DNA Detection by Hybridisation

DNA was also detected by hybridisation. 120 nm FNDs were DNA functionalized by click chemistry, as shown in FIG. 2. They then bind to biotin-modified model DNA sequences, which in turn bind to the lateral flow strip. This gives a LoD of 400 fM for 120 nm FNDs, as shown in FIG. 8.

Example 5—Protein Sandwich Detection

Protein detection was demonstrated using a p24 HIV capsid protein for HIV diagnostics. FNDs were functionalized with anti-HIV antibody. This binds to p24 in a sandwich format with a VHH-biotin anti-p24 nanobody, which binds to the lateral flow test.[27] This assay is currently limited by the affinity reaction between the FND-anti-HIV and the p24 (current LoD of 100 pg/mL), due to the low concentrations of FNDs used to reduce background. Various techniques are being explored to improve this, such as the use of a second VHH on the FNDs (Table 1).

Further Embodiments

1. An in vitro diagnostic assay method, comprising:
   providing a sample which may comprise target analyte(s);
   contacting the sample with a fluorescent label whose fluorescence can be externally modulated, such that the fluorescent label is associated with target analyte(s), if present, to form a fluorescent label-analyte complex; and
   detecting the fluorescent label-analyte complex.
2. Assay method according to 1, further comprising:
   a) exciting the fluorescent label using a suitable light source, and detecting the resulting fluorescence;
   b) modulating the fluorescence of the fluorescent label and detecting the resulting fluorescence to obtain a fluorescence time series comprising the fluorescence results from steps a) and b); and
   c) optionally repeating the modulation step one or more times and detecting the resulting fluorescence to obtain a fluorescence time series comprising the fluorescence results from steps a), b) and c).

3. Assay method according to 2, which comprises applying a frequency domain analysis to the fluorescence time series acquired in step b) or c).
4. Assay method according to 3, wherein the frequency domain analysis comprises applying a lock-in amplification algorithm or Fourier transform to the fluorescence time series.
5. Assay method according to any one of the above 2 to 4, wherein the detection of the fluorescence in each step comprises acquiring an image, spectrum or photon count.
6. Assay method according to any one of the above 2 to 5, comprising analysing the fluorescence time series acquired in step b) or c) to detect and/or quantify the presence of the target analyte(s).
7. Assay method according to any one of the above 1 to 6, wherein the fluorescent label comprises a material having a nitrogen vacancy centre.
8. Assay method according to 7, wherein the material having a nitrogen vacancy centre comprises fluorescent nanodiamonds (FNDs).
9. Assay method according to 8, wherein the FNDs comprise a hydrophilic layer.
10. Assay method according to 9, wherein the hydrophilic layer comprises a hydrophilic polymer.
11. Assay method according to 8, wherein the hydrophilic polymer comprises polyglycerol (PG) or polyethylene glycol (PEG).
12. Assay method according to any one of the above 1 to 11, wherein the FNDs comprise probe(s) suitable for associating with the target analyte(s).
13. Assay method according to 12, wherein said probe(s) comprise a peptide, protein, antibody, nucleic acid, oligonucleotide, aptamer, DNA, RNA, carbohydrate, small molecule (for example hormone, steroid, drug, small molecule less than 100 kDa) or cell.
14. Assay method according to 12 or 13, wherein the FNDs comprise a hydrophilic layer as defined in any one of the above 9 to 11, and wherein said probe(s) are attached to the hydrophilic layer via a suitable surface group.
15. Assay method according to any one of the above 1 to 14, wherein the assay method comprises a microfluidic flow assay, ELISA, qPCR, microarray, isothermal amplification, dot-blot, flow cytometry or fluorescence-activated cell sorting (FACS).
16. Assay method according to any one of the above 1 to 15, wherein the sample is applied to a solid phase.
17. Assay method according to 16, wherein the solid phase comprises a multiwell plate, beads, column, photonic device, microfluidic chip or capillary bed for microfluidic flow assay.
18. Assay method according to 17, wherein the capillary bed for microfluidic flow assay comprises a microfluidic or porous material selected from paper, nitrocellulose, cellulose, nylon, silk, polyvinylidine fluoride (PVDF), polydimethylsiloxane (PDMS), silicon and glass.
19. Assay method according to any one of the above 15 to 18, wherein the microfluidic flow assay comprises lateral flow, dip-stick, vertical flow or microfluidic channels.
20. Assay method according to any one of the above 1 to 19, which is a lateral flow assay or vertical flow assay.
21. Assay method according to any one of the above 2 to 20, wherein the fluorescence of the fluorescent label is modulated by a magnetic field, electric field, microwave field or electromagnetic radiation at near infrared or deep red wavelength.

22. Assay method according to 21, wherein the fluorescence of the fluorescent label is modulated by a microwave field or a magnetic field.

23. Assay method according to 21 or 22, wherein the fluorescent label comprises a nitrogen vacancy centre, and a microwave resonator with resonant frequency of 1-40 GHz is used to enhance the coupling between the label and the applied modulated microwaves.

24. Assay method according to 23, wherein the microwave resonator provides a uniform peak microwave magnetic field amplitude across the label.

25. Assay method according to any one of the above 1 to 24, wherein the target analyte(s) comprise a biomarker for disease diagnosis, monitoring or progression, therapeutic drug monitoring, vaccination coverage and vaccine efficacy, forensics, environmental monitoring, foodborne or plant pathogens, serology, monitoring disease treatment, and/or defence applications.

26. Assay method according to 25, wherein the target analyte(s) comprise a peptide, protein, antibody, antigen, carbohydrate, glycopeptide, cell, bacterium, nucleic acid, DNA, RNA aptamer, cytokine and/or small molecule, preferably wherein the analyte(s) comprise an antibody, antigen, DNA or RNA.

27. A device for performing an in vitro diagnostic assay, wherein said device comprises:
a solid phase comprising a fluorescent label whose fluorescence can be externally modulated;
an excitation light source;
a fluorescence modulator; and
a fluorescence detector.

28. Device according to 27, further comprising a controller/processing unit, preferably configured to apply frequency-domain analysis to the results obtained from fluorescence detection.

29. Device according to 28, wherein the controller/processing unit is configured to apply a lock-in algorithm or Fourier Transform to the results obtained from fluorescence detection.

30. Device according to any one of the above 27 to 29, wherein:
the fluorescence detector comprises a portable reader; and/or
the fluorescence modulator comprises a microwave signal generator.

31. Device according to 30, further comprising a microwave resonator with resonant frequency of 1-40 GHz.

32. Device according to 30, wherein the portable reader comprises a smartphone, tablet or other connected device.

33. Device according to any one of the above 27 to 32, wherein the fluorescent label comprises a material having a nitrogen vacancy centre.

34. Device according to 33 wherein the material having a nitrogen vacancy centre comprises fluorescent nanodiamonds (FNDs) as defined in any one of the above 8 to 14.

35. Device according to any one of the above 27 to 34, wherein the solid phase is as defined in 17 or 18.

36. Device according to any one of the above 27 to 35, comprising a lateral flow assay or vertical flow assay.

37. A kit for performing an in vitro diagnostic assay, wherein said kit comprises:
a solid phase comprising a fluorescent label whose fluorescence can be externally modulated, or
a solid phase and a separate liquid suspension or solution comprising a fluorescent label whose fluorescence can be externally modulated.

38. A kit according to 37, further comprising:
an excitation light source;
a fluorescence modulator; and
a fluorescence detector.

39. A solid phase comprising a fluorescent label whose fluorescence can be externally modulated, wherein said solid phase is selected from a multiwell plate, beads, column, photonic device, microfluidic chip or capillary bed for microfluidic flow assay.

40. Solid phase according to 39, wherein the capillary bed for microfluidic flow assay comprises a microfluidic or porous material selected from paper, nitrocellulose, cellulose, nylon, silk, polyvinylidine fluoride (PVDF), polydimethylsiloxane (PDMS), silicon and glass.

41. Solid phase according to 39 or 40, wherein the microfluidic flow assay comprises lateral flow, dipstick, vertical flow or microfluidic channels.

42. Solid phase according to 41, which is a lateral flow assay or vertical flow assay.

43. Solid phase according to any one of the above 39 to 42, wherein the fluorescent label comprises a material having a nitrogen vacancy centre.

44. Solid phase according to 43 wherein the material having a nitrogen vacancy centre comprises fluorescent nanodiamonds (FNDs) as defined in any one of the above 8 to 14.

REFERENCES

[1] J. G. Walter, F. Stahl, M. Reck, I. Praulich, Y. Nataf, M. Hollas, K. Pflanz, D. Melzner, Y. Shoham, T. Scheper, *Eng. Life Sci.* 2010, 10, 103-108.

[2] X. Gong, J. Cai, B. Zhang, Q. Zhao, J. Piao, W. Peng, W. Gao, D. Zhou, M. Zhao, J. Chang, *J. Mater. Chem. B* 2017, 5, 5079-5091.

[3] M. He, Z. Liu, *Anal. Chem.* 2013, 85, 11691-11694.

[4] A. S. Paterson, B. Raja, V. Mandadi, B. Townsend, M. Lee, A. Buell, B. Vu, J. Brgoch, R. C. Willson, *Lab Chip* 2017, 17, 1051-1059.

[5] L. Zhao, Y. Nakae, H. Qin, T. Ito, T. Kimura, H. Kojima, L. Chan, N. Komatsu, Beilstein *J. Org. Chem.* 2014, 10, 707-713.

[6] J. Kong, S. Yu, *Acta Biochim. Biophys. Sin.* (Shanghai). 2007, 39, 549-559.

[7] S. J. Yu, M. W. Kang, H. C. Chang, K. M. Chen, Y. C. Yu, *J. Am. Chem. Soc.* 2005, 127, 17604-17605.

[8] V. N. Mochalin, O. Shenderova, D. Ho, Y. Gogotsi, *Nat. Nanotechnol.* 2011, 7, 11-23.

[9] O. A. Shenderova, G. E. McGuire, *Biointerphases* 2015, 10, 030802.

[10] Y. Wu, T. Weil, *Phys. Sci. Rev.* 2017, 2, DOI 10.1515/psr-2016-0104.

[11] Y.-R. Chang, H.-Y. Lee, K. Chen, C.-C. Chang, D.-S. Tsai, C.-C. Fu, T.-S. Lim, Y.-K. Tzeng, C.-Y. Fang, C.-C. Han, et al., *Nat. Nanotechnol.* 2008, 3, 284-288.

[12] J.-P. Boudou, P. a Curmi, F. Jelezko, J. Wrachtrup, P. Aubert, M. Sennour, G. Balasubramanian, R. Reuter, A. Thorel, E. Gaffet, *Nanotechnology* 2009, 20, 235602.

US 12,669,507 B2

21

[13]S. K. Sarkar, A. Bumb, X. Wu, K. a Sochacki, P. Kellman, M. W. Brechbiel, K. C. Neuman, *Biomed. Opt. Express* 2014, 5, 1190-202.

[14]R. Chapman, T. Plakhoitnik, *Opt. Lett.* 2013, 38, 1847.

[27]E. R. Gray, J. C. Brookes, C. Caillat, V. Turbe, B. L. J. Webb, L. A. Granger, B. S. Miller, L. E. McCoy, M. El Khattabi, C. T. Verrips, et al., *ACS Infect. Dis.* 2017, 3, DOI 10.1021/acsinfecdis.6b00189.

SEQUENCE LISTING

```
<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: 5' Amino Modifier C6

<400> SEQUENCE: 1
agcgaccgtt cgtcgtacgc tcggac                                          26

<210> SEQ ID NO 2
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: 5' biotin modification
<220> FEATURE:
<221> NAME/KEY: misc_feature
<223> OTHER INFORMATION: 3' digoxigenin modification

<400> SEQUENCE: 2
gtccgagcgt acgacgaacg tcgct                                           26
```

[15]R. Igarashi, Y. Yoshinari, H. Yokota, T. Sugi, F. Sugihara, K. Ikeda, H. Sumiya, S. Tsuji, I. Mori, H. Tochio, et al., *Nano Lett.* 2012, 12, 5726-5732.

[16]A. Hegyi, E. Yablonovitch, *Nano Lett.* 2013, 13, 1173-1178.

[17]L. V. Doronina-Amitonova, I. V. Fedotov, A. M. Zheltikov, *Opt. Lett.* 2015, 40, 725.

[18]J. Leis, P. Martin, D. Buttsworth, *Electron. Lett.* 2012, 48, 259.

[19]C.-C. Fu, H.-Y. Lee, K. Chen, T.-S. Lim, H.-Y. Wu, P.-K. Lin, P.-K. Wei, P.-H. Tsao, H.-C. Chang, W. Fann, *Proc. Natl. Acad. Sci.* 2007, 104, 727-732.

[20]A. C. Taylor, C. H. Gonzilez, B. S. Miller, R. J. Edgington, P. Ferretti, R. B. Jackman, *Sci. Rep.* 2017, 7, DOI 10.1038/s41598-017-07361-y.

[21]A. Bumb, S. K. Sarkar, N. Billington, M. W. Brechbiel, K. C. Neuman, *J. Am. Chem. Soc.* 2013, 135, 7815-7818.

[22]A. Krueger, J. Stegk, L. Lu, G. Jarre, 2014, 7-8.

[23]Y. Zeng, W. Liu, Z. Wang, S. Singamaneni, R. Wang, *Langmuir* 2018, 34, 4036-4042.

[24]T. Zhang, A. Neumann, J. Lindlau, Y. Wu, G. Pramanik, B. Naydenov, F. Jelezko, F. Schuder, S. Huber, M. Huber, et al., *J. Am. Chem. Soc.* 2015, 137, 9776-9779.

[25]G. T. Hermanson, G. T. Hermanson, in *Bioconjugate Tech.*, 2013, pp. 275-298.

[26]D. A. Armbruster, T. Pry, *Clin. Biochem. Rev.* 2008, 29 Suppl 1, S49-52.

The invention claimed is:

1. An in vitro diagnostic assay method, comprising:
providing a sample which may comprise target analyte(s);
contacting the sample with a fluorescent label whose fluorescence can be externally modulated, such that the fluorescent label is associated with target analyte(s), if present, to form a fluorescent label-analyte complex; and
detecting the fluorescent label-analyte complex;
wherein said fluorescent label is a material which contains a nitrogen vacancy center;
wherein the method further comprises:
a) exciting the fluorescent label using a suitable light source, and detecting the resulting fluorescence;
b) modulating the fluorescence of the fluorescent label and detecting the resulting fluorescence to obtain a fluorescence time series comprising the fluorescence results from steps a) and b); and
c) optionally repeating the modulation step one or more times and detecting the resulting fluorescence to obtain a fluorescence time series comprising the fluorescence results from steps a), b) and c); and
wherein the sample is applied to a solid phase comprising a multiwell plate, beads, column, photonic device, microfluidic chip or capillary bed for microfluidic flow assay;
further wherein the assay method comprises a microfluidic flow assay, ELISA, qPCR, microarray, isothermal amplification, dot-blot, flow cytometry, fluorescence-activated cell sorting (FACS), a lateral flow assay or a vertical flow assay.

2. Assay method according to claim 1, which comprises applying a frequency domain analysis to the fluorescence time series acquired in step b) or c), optionally wherein the frequency domain analysis comprises applying a lock-in amplification algorithm or Fourier transform to the fluorescence time series.

3. Assay method according to claim 1, wherein said material which contains a nitrogen vacancy center comprises fluorescent nanodiamonds (FNDs).

4. Assay method according to claim 3, wherein the FNDs comprise a hydrophilic layer comprising a hydrophilic polymer, optionally wherein the hydrophilic polymer comprises polyglycerol (PG) or polyethylene glycol (PEG).

5. Assay method according to claim 3, wherein the FNDs comprise probe(s) suitable for associating with the target analyte(s), optionally wherein said probe(s) comprise a protein.

6. Assay method according to claim 1, wherein the fluorescence of the fluorescent label is modulated by a microwave field or a magnetic field, wherein the fluorescent label comprises a nitrogen vacancy center, and a microwave resonator with resonant frequency of 1-40 GHz is used to enhance the coupling between the label and the applied modulated microwaves.

*     *     *     *     *